(12) United States Patent
Sanders et al.

(10) Patent No.: US 11,559,631 B2
(45) Date of Patent: *Jan. 24, 2023

(54) SAFETY NEEDLE DEVICE

(71) Applicant: Becton, Dickinson and Company, Franklin Lakes, NJ (US)

(72) Inventors: Laurie Sanders, Glen Ridge, NJ (US); Darrin Swanson, Randleman, NC (US); John Hayes, Raleigh, NC (US); Gretchen Willard, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 390 days.

This patent is subject to a terminal disclaimer.

(21) Appl. No.: 16/818,350

(22) Filed: Mar. 13, 2020

(65) Prior Publication Data
US 2020/0215272 A1  Jul. 9, 2020

Related U.S. Application Data

(63) Continuation of application No. 15/837,008, filed on Dec. 11, 2017, now Pat. No. 10,589,036.
(Continued)

(51) Int. Cl.
*A61M 5/32* (2006.01)
*A61M 25/06* (2006.01)

(52) U.S. Cl.
CPC ........ *A61M 5/3271* (2013.01); *A61M 5/3204* (2013.01); *A61M 5/326* (2013.01);
(Continued)

(58) Field of Classification Search
CPC .............. A61M 5/3243; A61M 5/3213; A61M 5/3202; A61M 5/326; A61M 5/3272;
(Continued)

(56) References Cited

U.S. PATENT DOCUMENTS

| | | |
|---|---|---|
| 3,367,488 A | 2/1968 | Hamilton |
| 3,869,062 A | 3/1975 | Jaeschke et al. |

(Continued)

FOREIGN PATENT DOCUMENTS

| | | |
|---|---|---|
| CA | 2551835 A1 | 8/2005 |
| CA | 2803761 A1 | 12/2011 |

(Continued)

OTHER PUBLICATIONS

Final Office Action in U.S. Appl. No. 15/837,748 dated Feb. 29, 2020, 19 pages.
(Continued)

*Primary Examiner* — Tiffany Legette
(74) *Attorney, Agent, or Firm* — Servilla Whitney LLC

(57) ABSTRACT

A safety needle device is disclosed having a housing configured to couple to a syringe, the housing having a proximal end, a distal end, and a housing body. A first guide path, a second guide path and a third guide path may be disposed on the housing body. A needle hub is disposed on the proximal end of the housing and a needle cannula is attached to the needle hub. The device having a retractable sheath configured to move between an initial position, a retracted position and an extended position with respect to the housing, wherein the initial position partially exposes a distal tip of the needle cannula, the retracted position fully exposes the needle cannula, and the extended position fully covers the distal tip of the needle cannula. The retractable sheath also may have a guide element. The first, second and third guide paths are configured to slidingly receive the guide element. The device also having a first locking member, a second locking member, a rotating cam disposed in the housing body, and a spring element to bias the retractable sheath to an extended state to cover the distal end of the needle cannula upon completion of an injection.

18 Claims, 9 Drawing Sheets

Related U.S. Application Data

(60) Provisional application No. 62/433,294, filed on Dec. 13, 2016.

(52) U.S. Cl.
CPC ........ *A61M 5/3243* (2013.01); *A61M 5/3257* (2013.01); *A61M 5/3272* (2013.01); *A61M 25/0606* (2013.01); *A61M 25/0618* (2013.01); *A61M 25/0625* (2013.01); *A61M 25/0631* (2013.01); *A61M 25/0637* (2013.01); *A61M 5/3269* (2013.01); *A61M 5/3275* (2013.01); *A61M 2005/325* (2013.01); *A61M 2005/3247* (2013.01); *A61M 2005/3258* (2013.01); *A61M 2005/3267* (2013.01); *A61M 2205/59* (2013.01)

(58) Field of Classification Search
CPC .............. A61M 5/3275; A61M 5/3269; A61M 25/0631; A61M 25/0637; A61M 25/0606; A61M 2005/3258; A61M 2005/325; A61M 2005/3247

See application file for complete search history.

(56) References Cited

U.S. PATENT DOCUMENTS

| | | |
|---|---|---|
| 4,610,667 A | 9/1986 | Pedicano et al. |
| 4,795,432 A | 1/1989 | Karczmer |
| 4,813,940 A | 3/1989 | Parry |
| 4,911,693 A | 3/1990 | Paris |
| 4,950,250 A | 8/1990 | Haber et al. |
| 5,084,028 A | 1/1992 | Kennedy et al. |
| 5,330,899 A | 7/1994 | Devaughn |
| 5,336,199 A | 8/1994 | Castillo et al. |
| 5,395,347 A | 3/1995 | Blecher et al. |
| 5,415,645 A | 5/1995 | Friend et al. |
| 5,591,138 A | 1/1997 | Vaillancourt |
| 5,688,241 A | 11/1997 | Asbaghi |
| 5,984,899 A | 11/1999 | D'Alessio et al. |
| RE36,885 E | 9/2000 | Blecher et al. |
| 6,884,237 B2 | 4/2005 | Asbaghi |
| 6,926,697 B2 | 8/2005 | Malenchek |
| 7,134,550 B2 | 11/2006 | Groth |
| 7,320,682 B2 | 1/2008 | Cocker et al. |
| 7,361,159 B2 | 4/2008 | Fiser et al. |
| 7,513,888 B2 | 4/2009 | Sircom et al. |
| 7,665,605 B2 | 2/2010 | Erickson et al. |
| 7,811,261 B2 | 10/2010 | Rubinstein et al. |
| 7,871,397 B2 | 1/2011 | Schraga |
| 8,048,036 B2 | 11/2011 | Woehr et al. |
| 8,062,265 B2 | 11/2011 | Millerd |
| 8,162,882 B2 | 4/2012 | Rubinstein et al. |
| 8,303,541 B2 | 11/2012 | Chun |
| 8,333,738 B2 | 12/2012 | Millerd |
| 8,439,870 B2 | 5/2013 | Moyer et al. |
| 8,496,627 B2 | 7/2013 | Chelak et al. |
| 8,636,688 B2 | 1/2014 | Shaw |
| 8,636,703 B2 | 1/2014 | Foshee et al. |
| 8,647,307 B2 | 2/2014 | Gratwohl et al. |
| 8,663,129 B2 | 3/2014 | Allen et al. |
| 8,747,355 B2 | 6/2014 | Rubinstein et al. |
| 8,827,961 B2 | 9/2014 | Emmott et al. |
| 8,968,241 B2 | 3/2015 | Liversidge |
| 8,979,794 B2 | 3/2015 | Chevallier |
| 9,050,416 B2 | 6/2015 | Feret et al. |
| 9,061,106 B2 | 6/2015 | Roberts et al. |
| 9,067,024 B2 | 6/2015 | Roberts et al. |
| 9,186,466 B2 | 11/2015 | Zachek et al. |
| 9,352,099 B2 | 5/2016 | Roberts et al. |
| 9,352,100 B2 | 5/2016 | Ward et al. |
| 9,352,101 B2 | 5/2016 | Roberts et al. |
| 9,370,327 B2 | 6/2016 | Teoh |
| 9,408,632 B2 | 8/2016 | Erskine |
| 9,445,760 B2 | 9/2016 | Allen et al. |
| 9,694,140 B2 | 7/2017 | Rubinstein et al. |
| 9,848,810 B2 | 12/2017 | Allen et al. |
| 2001/0031949 A1 | 10/2001 | Asbaghi |
| 2002/0063074 A1 | 5/2002 | Simm et al. |
| 2002/0165497 A1 | 11/2002 | Greene |
| 2003/0093009 A1 | 5/2003 | Newby et al. |
| 2003/0120209 A1 | 6/2003 | Jensen et al. |
| 2003/0121815 A1 | 7/2003 | Bergeron et al. |
| 2003/0181867 A1 | 9/2003 | Bressler et al. |
| 2003/0181869 A1 | 9/2003 | Swenson et al. |
| 2005/0067309 A1 | 3/2005 | Choi |
| 2005/0113750 A1* | 5/2005 | Targell ................ A61M 5/3272 604/110 |
| 2005/0119627 A1 | 6/2005 | Crawford |
| 2005/0279664 A1 | 12/2005 | Hommann |
| 2006/0189933 A1 | 8/2006 | Alheidt et al. |
| 2006/0189934 A1* | 8/2006 | Kuracina ......... A61B 5/150641 604/110 |
| 2006/0213793 A1 | 9/2006 | Brand |
| 2009/0024093 A1 | 1/2009 | Carrel et al. |
| 2009/0254042 A1 | 10/2009 | Gratwohl et al. |
| 2009/0299295 A1* | 12/2009 | Rubinstein ............ A61M 5/422 604/198 |
| 2010/0298770 A1 | 11/2010 | Rubinstein et al. |
| 2011/0288491 A1 | 11/2011 | Newman et al. |
| 2011/0319817 A1 | 12/2011 | Rubinstein et al. |
| 2012/0029440 A1 | 2/2012 | Boyd et al. |
| 2014/0048433 A1 | 2/2014 | Dasbach et al. |
| 2014/0097111 A1 | 4/2014 | Dasbach et al. |
| 2014/0013570 A1 | 5/2014 | Rubinstein et al. |
| 2014/0228772 A1 | 8/2014 | Ward et al. |
| 2014/0364803 A1 | 12/2014 | Rubinstein et al. |
| 2015/0034516 A1 | 2/2015 | Chapin et al. |
| 2015/0094659 A1 | 4/2015 | Schraga |
| 2015/0165132 A1 | 6/2015 | Perot et al. |
| 2015/0182704 A1 | 7/2015 | Chevallier |
| 2015/0190580 A1 | 7/2015 | Imai et al. |
| 2015/0190586 A1 | 7/2015 | Takemoto |
| 2015/0297837 A1 | 10/2015 | Schraga |
| 2015/0297881 A1 | 10/2015 | Sanders et al. |
| 2016/0074572 A1 | 3/2016 | Spool et al. |
| 2016/0303331 A1 | 10/2016 | Evans et al. |
| 2017/0106136 A1 | 4/2017 | Dibiasi |
| 2017/0233168 A1 | 8/2017 | Horvath et al. |
| 2018/0161490 A1 | 6/2018 | Sanders et al. |
| 2018/0161492 A1 | 6/2018 | Sanders et al. |
| 2018/0161521 A1 | 6/2018 | Sanders et al. |

FOREIGN PATENT DOCUMENTS

| | | |
|---|---|---|
| CN | 103079610 A | 5/2013 |
| EP | 0409180 A1 | 1/1991 |
| EP | 0734739 A2 | 10/1996 |
| EP | 0750915 A2 | 1/1997 |
| EP | 1537890 A1 | 6/2005 |
| EP | 1949928 A1 | 7/2008 |
| EP | 2298397 A1 | 3/2011 |
| EP | 2585146 B1 | 3/2017 |
| FR | 2884723 A1 | 10/2006 |
| FR | 2930160 A1 | 10/2009 |
| GB | 2437923 A | 11/2007 |
| JP | H03139363 A | 6/1991 |
| JP | 2007519474 A | 7/2007 |
| JP | 2010502316 A | 1/2010 |
| JP | 2012500063 A | 1/2012 |
| JP | 2013523197 A | 6/2013 |
| JP | 2013529973 A | 7/2013 |
| MX | 2013/000081 | 3/2013 |
| MX | 349289 B | 7/2017 |
| WO | 92/06725 A1 | 4/1992 |
| WO | 02/11797 A1 | 2/2002 |
| WO | 03/045480 A1 | 6/2003 |
| WO | 2008028305 A1 | 3/2008 |
| WO | 2008050158 A2 | 5/2008 |
| WO | 2009040602 A1 | 4/2009 |
| WO | 2009/114777 A1 | 9/2009 |
| WO | 2010/033767 A2 | 3/2010 |
| WO | 2011/107330 A1 | 9/2011 |

(56) References Cited

FOREIGN PATENT DOCUMENTS

| WO | 2012/000833 | A1 | 1/2012 |
| WO | 2012000833 | A1 | 1/2012 |
| WO | 2012/013587 | A1 | 2/2012 |
| WO | 2015/164416 | A1 | 10/2015 |
| WO | 2016/087187 | A1 | 6/2016 |

OTHER PUBLICATIONS

Final Office Action in U.S. Appl. No. 15/837,756 dated Feb. 28, 2020, 34 pages.
Final Office Action in U.S. Appl. No. 15/837,810 dated Feb. 28, 2020, 24 pages.
Final Office Action in U.S. Appl. No. 15/837,018 dated Jun. 18, 2019, 15 pages.
Non-Final Office Action in U.S. Appl. No. 15/837,008 dated Jul. 25, 2019, 23 pages.
Non-Final Office Action in U.S. Appl. No. 15/837,011 dated Oct. 7, 2019, 8 pages.
Non-final Office Action in U.S. Appl. No. 15/837,012 dated Aug. 16, 2019, 14 pages.
Non-Final Office Action in U.S. Appl. No. 15/837,018 dated Dec. 5, 2019, 14 pages.
Non-Final Office Action in U.S. Appl. No. 15/837,020 dated Feb. 3, 2020, 11 pages.
Non-Final Office Action in U.S. Appl. No. 15/837,748 dated Oct. 17, 2019, 19 pages.
Non-Final Office Action in U.S. Appl. No. 15/837,756 dated Oct. 17, 2019, 39 pages.
Non-Final Office Action in U.S. Appl. No. 15/837,810 dated Oct. 17, 2019, 27 pages.
PCT International Preliminary Report on Patentability in PCT/US2017/065688 dated Jun. 27, 2019, 9 pages.
PCT International Preliminary Report on Patentability in PCT/US2017/065689 dated Jun. 27, 2019, 10 pages.
PCT International Preliminary Report on Patentability in PCT/US2017/065692 dated Jun. 27, 2019, 8 pages.
PCT International Preliminary Report on Patentability in PCT/US2017/065693 dated Jun. 27, 2019, 7 pages.
PCT international Preliminary Report on Patentability in PCT/US2017/065716 dated Jun. 27, 2019, 9 pages.
PCT International Preliminary Report on Patentability in PCT/US2017/065717 dated Jun. 27, 2019, 9 pages.
PCT International Preliminary Report on Patentability in PCT/US2017/065718 dated Jun. 27, 2019, 12 pages.
PCT International Search Report and Written Opinion in PCT/US2017/065688 dated Feb. 26, 2018, 13 pages.
PCT International Search Report and Written Opinion in PCT/US2017/065689, dated Jan. 2, 2019, 18 pages.
PCT International Search Report and Written Opinion in PCT/US2017/065691 dated Mar. 27, 2018, 14 pages.
PCT International Search Report and Written Opinion in PCT/US2017/065692 dated Mar. 13, 2018, 14 pages.
PCT International Search Report and Written Opinion in PCT/US2017/065693 dated Mar. 7, 2018, 12 pages.
PCT International Search Report and Written Opinion in PCT/US2017/065716 dated Mar. 21, 2018, 14 pages.
PCT International Search Report and Written Opinion in PCT/US2017/065717 dated Mar. 19, 2018, 12 pages.
PCT International Search Report and Written Opinion in PCT/US2017/065718 dated Jan. 2, 2019, 18 pages.
PCT invitation to Pay Additional Fees and, Where Applicable, Protest Fee in PCT/US2017/065689 dated Feb. 20, 2018, 12 pages.
PCT Invitation to Pay Additional Fees, and, Where Applicable, Protest Fee in PCT/US2017/065718 dated Apr. 9, 2018, 13 pages.

* cited by examiner

SAFETY NEEDLE DEVICE

CROSS-REFERENCE TO RELATED APPLICATIONS

This application is a continuation of U.S. patent application Ser. No. 15/837,008, filed on Dec. 11, 2017, issued as U.S. Pat. No. 10,589,036 on Mar. 17, 2020, which claims priority under 35 U.S.C. § 119(e) to U.S. Provisional Application No. 62/433,294, filed Dec. 13, 2016, the disclosures of which are incorporated herein by reference in their entirety.

TECHNICAL FIELD

The present disclosure relates generally to a safety needle device, and more particularly to a single-use passive safety needle device having a housing, a first guide path, a second guide path, a third guide path intersecting the first guide path and the second guide path, a needle hub, a needle cannula, a retractable sheath, a first locking member, a second locking member, a rotating cam, and a spring to bias the retractable sheath in a distal direction to cover the distal end of the needle cannula.

BACKGROUND

Needle devices are used throughout the medical industry for the injection and withdrawal of a wide variety of fluids and solutions into and from the human body. Because of the numerous potential hazards associated with the handling and manipulation of bodily fluids, and particularly blood, there are a number of known safety features that are frequently incorporated into various types of needle devices to protect the practitioner from accidental exposure to the needle.

Prior safety needle devices include several disadvantages including having a retractable sheath requiring long stroke distances to activate the safety feature, multi-component retraction and locking elements, and conveying an undesirable significant force against a patient's skin during activation of the safety feature upon receiving an injection. Conventional retraction syringe assemblies often also do not incorporate reuse prevention features, and thus, the retraction mechanism of the syringe may be reset so the syringe barrel may be reused. The reuse of syringe assemblies without sterilization or sufficient sterilization is believed to facilitate the transfer of contagious diseases. Further, the retraction features of conventional syringes may also require the user to actively activate the retraction mechanism. Accordingly, the chance of human error in failure to activate or properly activate the retraction mechanism can lead to continued exposure of needles leading to needle stick injuries.

Some known retracting sheath safety needle devices have been developed to include a single-use safety needle device assembly that obscures a substantial majority or an entirety of an injection needle from view before, during, and after an injection procedure. However, many injection procedures require that the practitioner know precisely the location and depth to which the needle is inserted in the patient's tissue to be sure that medication is delivered to an appropriate location. In addition, there exists a tendency for many users to falsely assume that they were "safe" from needle stick injuries, even in the non-locked initial state, due to the tip of the prior art retracting sheath safety needle devices being fully covered in an unlocked state.

Thus, there is a need in the art to provide a safety needle device having a passive activation mechanism that overcomes the deficiencies of the known retracting sheath safety needle devices and which allows for shorter stroke distance, ease of use, increased patient comfort, low part count, low part complexity, relatively compact design, and clear and unobstructed view of needle in an initial position.

SUMMARY

One aspect of the present disclosure pertains to a safety needle device including a housing configured to couple to a syringe, the housing having a proximal end, a distal end, and a housing body. The safety needle device also includes a first guide path, a second guide path and a third guide path disposed on the housing body, the second guide path intersecting the first guide path and the third guide path. In one or more embodiments, the one or more guide paths may be straight paths, and one or more guide paths may be helical. In one or more embodiments, the two guide paths may be straight paths, and one guide paths may be helical. In one or more embodiments, the first and third guide paths may be straight paths, and the second guide path may be helical. A needle hub is disposed on the proximal end of the housing with a needle cannula attached to the needle hub. The safety needle device may also include a retractable sheath having a guide element configured to move between an initial position, a retracted position and an extended position with respect to the housing, wherein the initial position partially exposes a distal tip of the needle cannula, the retracted position fully exposes the needle cannula, and the extended position fully covers the distal tip of the needle cannula. The first guide path and the second guide path are disposed on the housing body configured to receive the guide element. The safety needle device also includes a first locking member, a second locking member; a rotating cam disposed in the housing body and connected to the retractable sheath; and a spring element. In one or more embodiments, the safety needle device is a single use device. In one or more embodiments, the safety needle device is a passively activated device in which the safety features provide post-injection needle shielding without additional intervention by the user.

In one or more embodiments, the first locking member may comprise a tab on a distal end of the retractable sheath and a locking rib on the housing. In one or more embodiments, the first locking member may comprise a locking rib on a distal end of the retractable sheath and a tab on the housing. Movement of the retractable sheath from the initial position to the retracted position may engage the locking rib of the housing to the tab on the distal end of the retractable sheath. The retractable sheath may rotate with respect to the housing during movement from the initial position to the retracted position. Rotation of the retractable sheath from the initial position to the retracted position may transfer the guide element of the retractable sheath from the first guide path on the housing to the third guide path on the housing via the second guide path. In one or more embodiments, the guide element may be a peg. In one or more embodiments, the retractable sheath translates from the initial position to the retracted position without impediment.

In one or more embodiments, movement of the retractable sheath from the retracted position to the extended position may engage the second locking member to a distal tip of the needle cannula. In one or more embodiments, the second locking member may be a metal latch.

In one or more embodiments, the first locking member may inhibit reuse of the device by inhibiting rotation of the retractable sheath. The second locking member may inhibit reuse of the device by inhibiting translation of the retractable sheath.

In one or more embodiments, the spring element biases the retractable sheath toward the extended position. The needle cannula may be obscured from view when the retractable sheath is in the extended position.

In one or more embodiments, the spring element is a coil spring.

DETAILED DESCRIPTION

Figure 1:
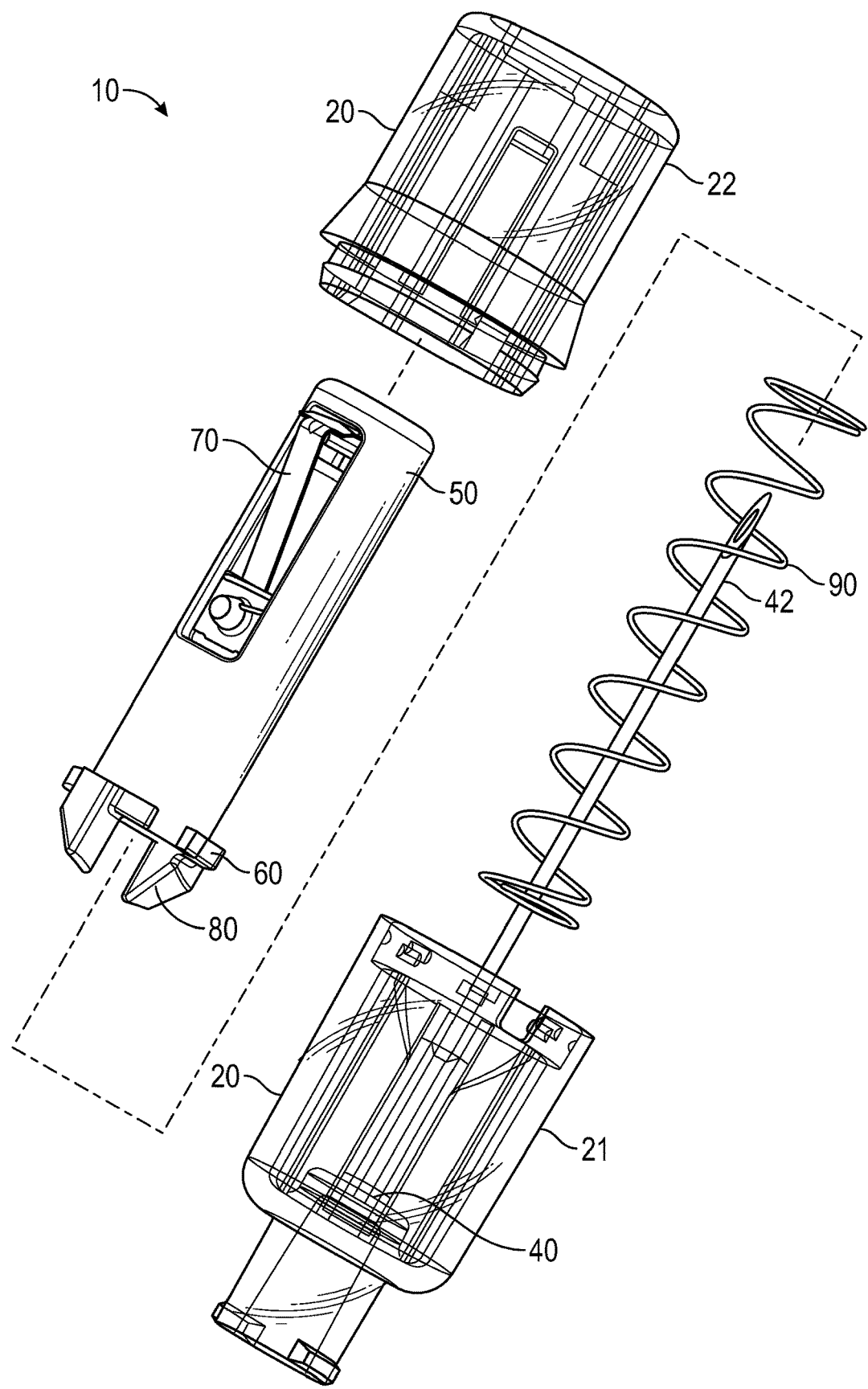
FIG. 1 illustrates an exploded view of a safety needle device according to a first embodiment.

Before describing several exemplary embodiments of the disclosure, it is to be understood that the disclosure is not limited to the details of construction or process steps set forth in the following description. The disclosure is capable of other embodiments and of being practiced or being carried out in various ways.

With respect to terms used in this disclosure, the following definitions are provided.

As used herein, the use of "a," "an," and "the" includes the singular and plural.

In this disclosure, a convention is followed wherein the distal end of the device is the end closest to a patient and the proximal end of the device is the end away from the patient and closest to a practitioner.

As used herein, a "safety needle device" refers to a device having a needle suitable for injection that includes one or more features to prevent needle stick injuries. As used herein, a "passive safety needle" refers to a safety needle device with a passive activation mechanism that automatically covers the distal end of the needle after a patient has been injected.

Reference to "syringe" includes syringes that are indicated for use with needles, nozzle, tubing, or for use in flush systems. As used herein, the term "syringe" refers to a simple pump-like device consisting of a plunger rod that fits tightly in a barrel or tube. The plunger rod can be pulled or pushed along inside the barrel, allowing the syringe to take in and expel a liquid or gas through an opening at the open end of the barrel. The open end of the syringe may be fitted with a needle, nozzle, or tubing to help direct the flow of fluid into and out of the barrel. The syringe may be sterile or unsterile, depending upon the needs of the technician.

Embodiments of the safety needle device of the present disclosure provides a passive activation mechanism that overcomes the deficiencies of the known retracting sheath safety needle devices by allowing for a shorter distance for lockout travel, ease of use, increased patient comfort, low part count, low part complexity, relatively compact design, and clear and unobstructed view of needle in an initial position.

FIGS. 1-9 illustrate an exemplary safety needle device 10 according to the present disclosure. Safety needle device 10 includes a housing 20 configured to couple to a syringe (not shown). Housing 20 having a proximal end 21, a distal end 22, a housing body 23 and an opening 24 located on the distal end. A first guide path 30, a second guide path 32 and a third guide path 34 are disposed on the housing body 23. First guide path 30 and third guide path 34 are generally parallel to a central axis which extends along the housing body 23. Second guide path 32 is positioned at an angle, curvature or taper relative to the axis and intersects the first guide path 30 and third guide path 34 thereby serving to separate the first guide path 30 and third guide path 34. Second guide path 32 permits the guide element 52 to shift between the first guide path 30 and third guide path 34. In one or more embodiments, the one or more guide paths may be straight paths, and one or more guide paths may be helical. In one or more embodiments, the two guide paths may be straight paths, and one guide paths may be helical. In one or more embodiments, the first and third guide paths may be straight paths, and the second guide path may be helical. In one or more embodiment, the first guide path 30, the second guide path 32 and the third guide path 34 are disposed on the inner diameter of the housing body 23 to prevent tampering. In one or more embodiment, the first guide path 30, the second guide path 32 and the third guide path 34 are disposed on the inner diameter of the housing body 23 so as not to obstruct needle cannula/needle tip visibility.

Housing 20 may be of a unitary construction or may be formed from a plurality of components. In one or more embodiments, a proximal end 21 and a distal end 22 of the housing 20 can be separate components that are joined using techniques, such as but not limited to sonic welding, adhesive, snap or press fitting, or the like.

As shown in FIG. 1, proximal end 21 of housing 20 couples to a retractable sheath 50 such that the retractable sheath 50 is configured to move along and at least partially rotate about a central axis. A channel and an aperture are included in the retractable sheath 50 in order to permit the needle cannula 42 and distal tip 44 of needle cannula 42 to pass therethrough.

Needle hub 40 is disposed on the proximal end 21 of the housing 20. Needle cannula 42 is attached to the needle hub 40. The proximal end of retractable sheath 50 includes a guide element 52 configured to move between an initial position, a retracted position and an extended position with respect to the housing 20, wherein the initial position partially exposes a distal tip 44 of the needle cannula 42, the retracted position fully exposes the needle cannula 42, and the extended position fully covers the distal tip 44 of the needle cannula 42. The term "retractable sheath" is intended to include any sort of tubular member and U-shaped member. The retractable sheath 50 is dimensioned to be compatible with the size and type of needle cannula 40 as will be appreciated by those skilled in the art. The housing 20 includes a housing body 23 with an internal hollow region in which the retractable sheath 50 may move in the proximal and distal direction. The first guide path 30, the second guide path 32 and third guide path 34 are disposed on the inside surface of housing body 23 configured to directing the retractable sheath 50 during movement. In one or more embodiments, the first path, second path and third path are configured to slidingly receive the guide element 52 of the retractable sheath 50.

In one or more embodiments, the proximal end 21 of the housing 20 may be connectable to a luer connection or other fluid connector. Retractable sheath 50 is slidably mounted and movable in the distal opening 24 of the housing body to slidably accommodate and encase needle cannula 42 projecting axially from housing 20. The distal end of retractable sheath 50 is generally flush with distal end 22 of housing 20.

As shown in FIG. 1, needle cannula 42 may be connected to a needle hub 40 disposed at the proximal end 21 of the housing 20 and having a blunted tip (not shown) or beveled tip (as shown in FIG. 1) at the distal tip 44 of needle cannula 42. The needle cannula 42 is disposed in the needle hub 40 in a manner as would be well understood in the art. The needle hub 40 may be integrally formed with the proximal end 21 of housing 20. Needle hub 40 may be configured to be removable or permanently attached to the syringe, or alternatively, needle hub 40 may be integrally formed with the syringe. For example, needle hub 40 may include internal or external threads or other suitable coupling, latching, or locking features such as tabs, slots, projections, pressure/snap fits, and the like, for removably coupling the safety device to a syringe. In some embodiments, the housing 20 includes a generally cylindrically reduced needle support 41 that extends axially from the needle hub 40 to support the needle cannula 42.

Housing 20 and/or needle hub 40 are in fluid communication with the needle cannula 42 to permitting fluid to pass between the syringe and the needle cannula 42.

Figure 2:
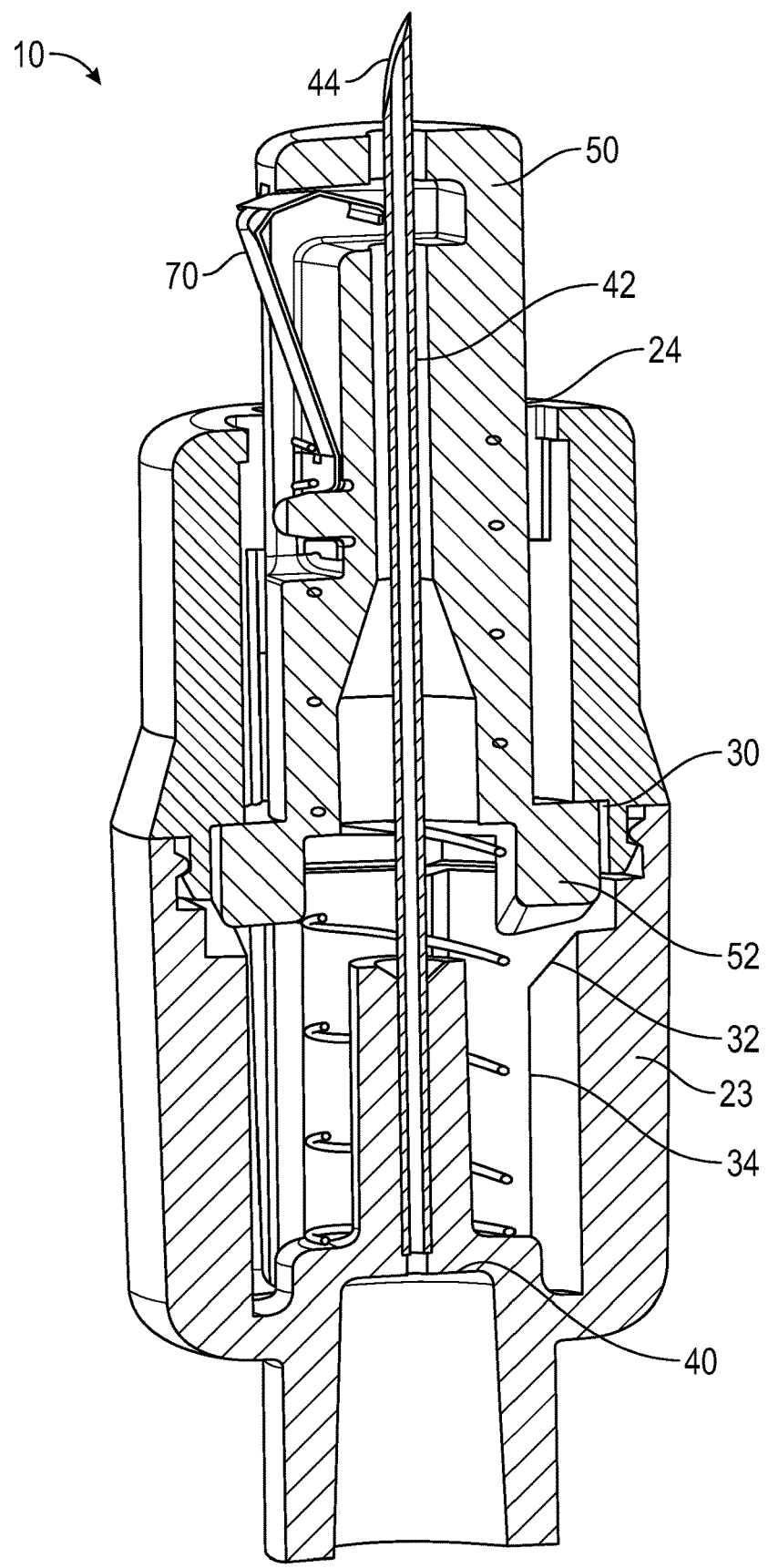
FIG. 2 illustrates a perspective view of a safety needle device shown in FIG. 1 in an initial state.
Figure 3:
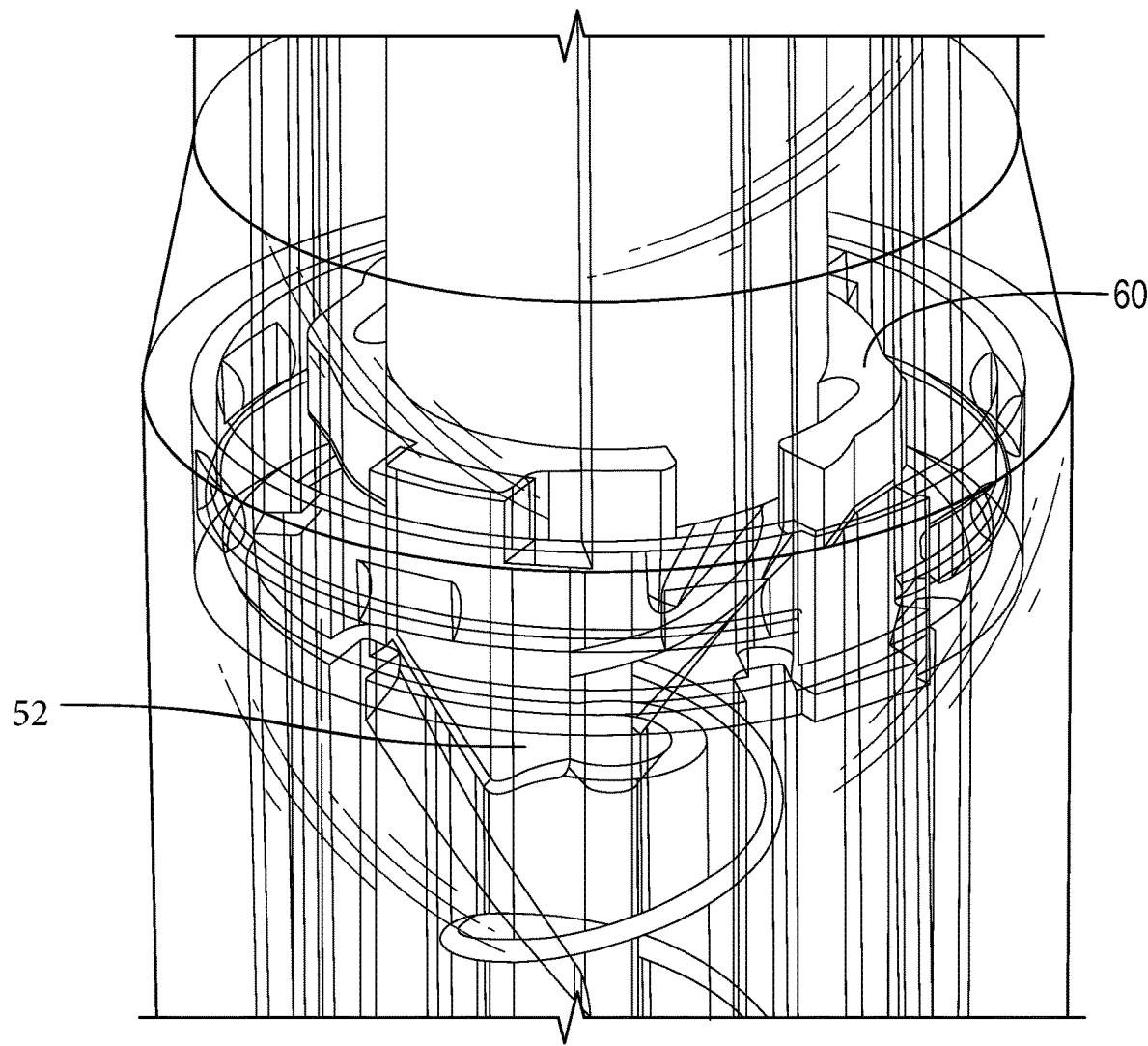
FIG. 3 illustrates a sectional view of a first locking element of the safety needle device shown in FIG. 1.
Figure 4:
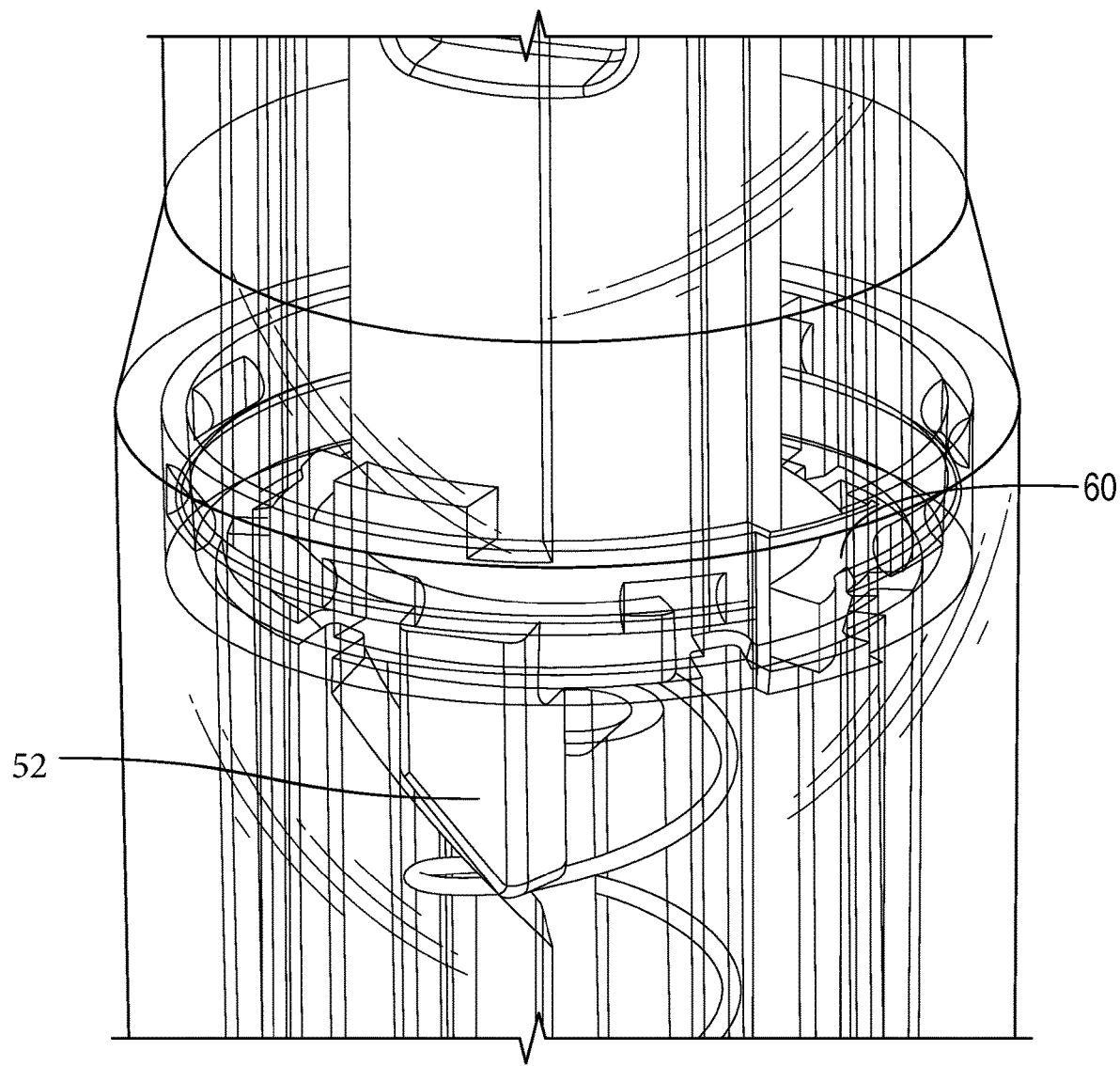
FIG. 4 illustrates another a sectional view of a first locking element of the safety needle device shown in FIG. 1.
Figure 5:
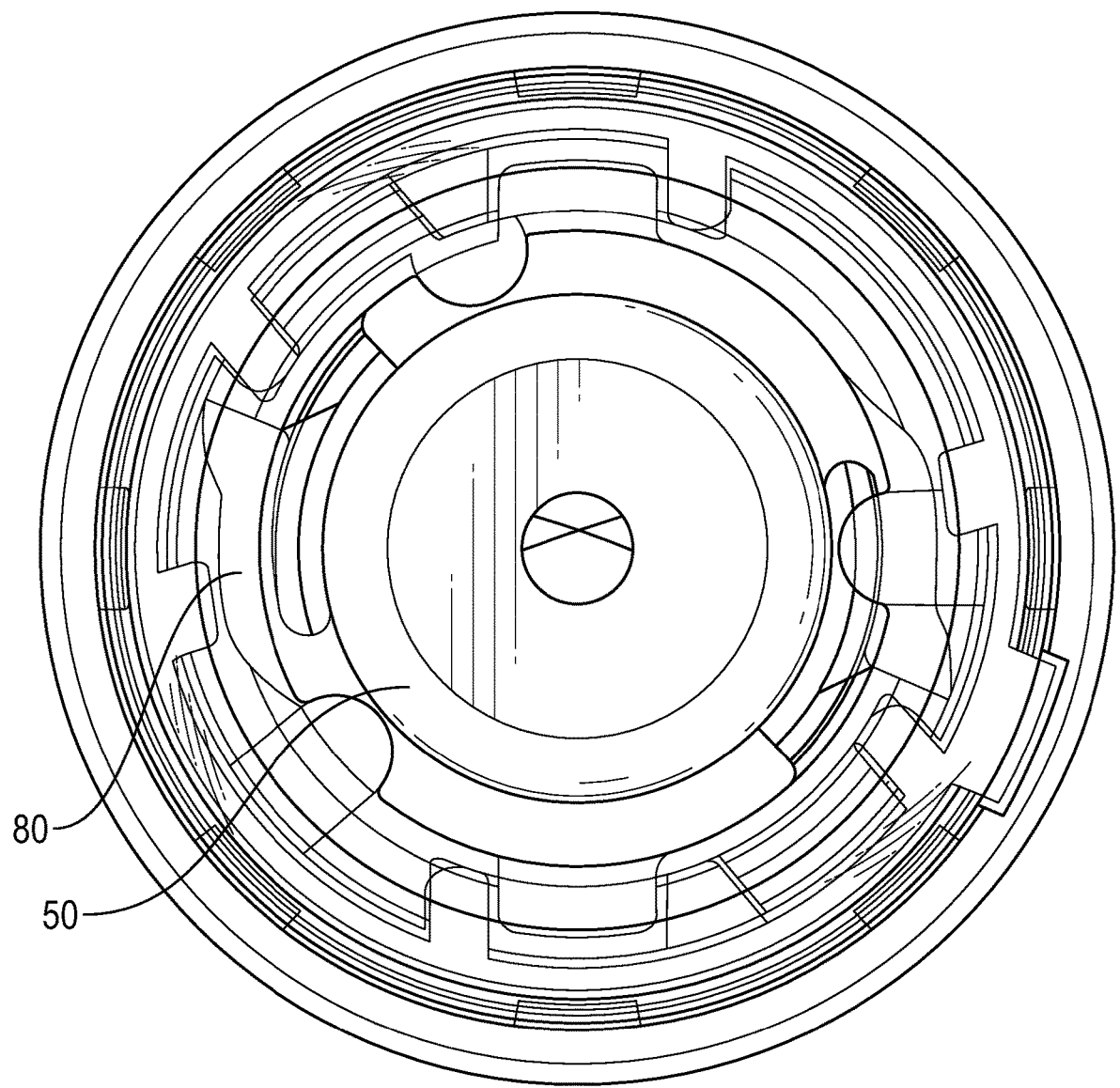
FIG. 5 illustrates a cross-sectional view of a safety needle device according to a first embodiment.
Figure 6:
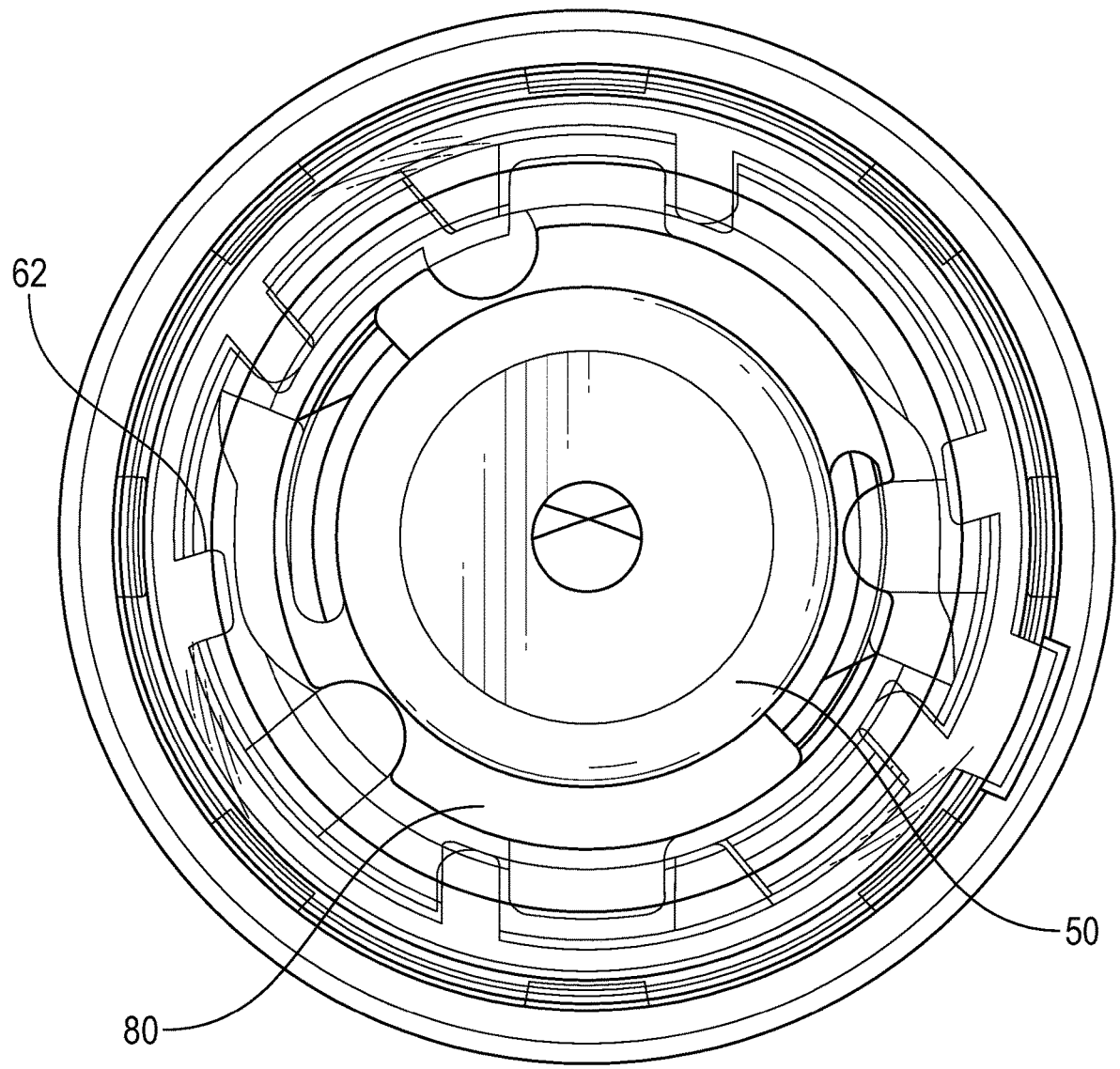
FIG. 6 illustrates another cross-sectional view of a safety needle device according to a first embodiment.

The needle cannula 42 extends from the needle hub 40 disposed in the housing 20 and extends to a distal tip 44. Distal tip 44 of the needle cannula 42 is partially exposed and protruding from the distal end of the retractable sheath 50 so as to be visible when the retractable sheath 50 is in an initial position, as shown in FIG. 2. The shaft of the needle cannula 42 is exposed from the retractable sheath 50 when the retractable sheath 50 is in a retracted position.

Figure 8:
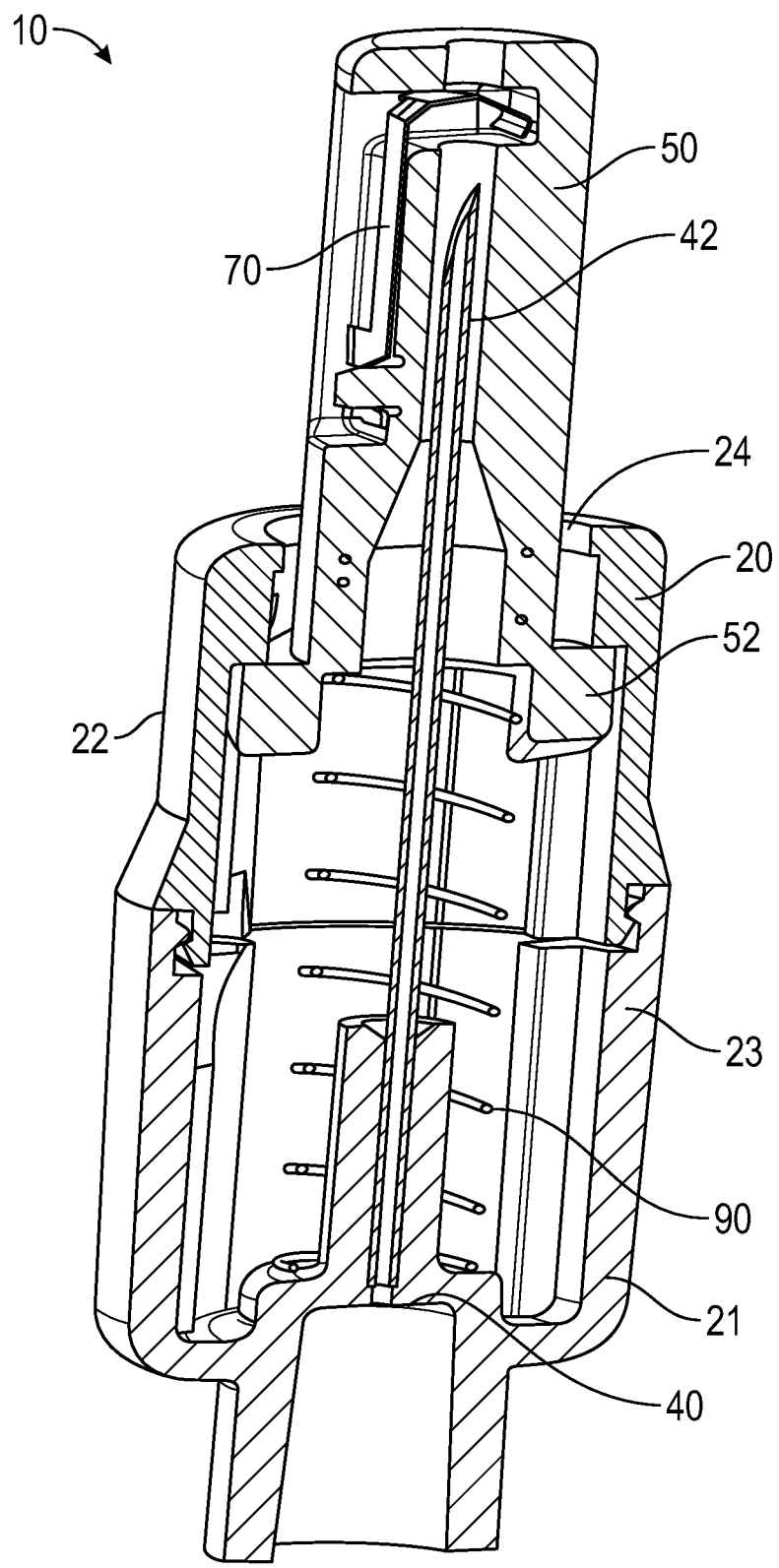
FIG. 8 illustrates a perspective view of a safety needle device shown in FIG. 1 in an extended state.

As illustrated in several of the drawings, most notably FIGS. 1 and 2, retractable sheath 50 is generally comprised of a tubular portion and is slidably retractable along the length of the needle cannula 42 such that a distal tip 44 of the needle cannula 42 is partially exposed and protruding from the distal end of the retractable sheath 50 when in an initial position so as to be visible to a user. A substantial or entire portion of needle cannula 42 is exposed when the retractable sheath 50 is in its retracted position. The length of needle cannula 42 which extends from the needle hub 40 in a distal direction is completely encased when retractable sheath 50 is in its extended position, as shown in FIG. 8.

The needle cannula 42 in accordance with the present disclosure can be formed from conventional materials such as steel or more preferably stainless steel. It will be realized by the skilled artisan that medical grade plastics, composites, ceramics, or like materials can be substituted.

The inside diameter of the retracting sheath 50 is selected so that it will fit closely over needle cannula 42. The retracting sheath 50 may be made of any suitable material, but preferably of a polymer which is tough enough to protect needle cannula 42.

The proximal end 51 of retractable sheath 50 includes a guide element 52 that extends radially outward from the proximal end of retractable sheath 50 and is configured to engage one or more paths formed on the inside surface of the housing body 23. In one or more embodiments, guide element 52 may be an outwardly extending peg that seats against a ledge of the distal end of the housing as shown in FIG. 2. As shown in FIGS. 1 and 2, housing 20 has an opening that receives the retractable sheath 50.

In one or more embodiments, retractable sheath 50 may be disposed and movable in the housing body 23. The retractable sheath 50 is spring loaded, and is supplied to the user with the retracting sheath 50 partially covering the needle cannula 42 so that the distal tip of the needle cannula is exposed and visible in an initial state, as shown in FIG. 2. In the initial state, the guide element 52 of the retractable sheath 50 is disposed in the first guide path of the housing body. In one or more embodiments, the guide element is a peg. Upon administration of the injection, the retractable sheath 50 moves from an initial position whereby the distal tip 44 of the needle cannula 42 is exposed to a retracted position whereby the needle cannula is increasingly exposed so that the needle cannula may penetrate the injection site. As shown in FIGS. 3-7, the retractable sheath 50 rotates with respect to the housing 20 by way of rotating cam 80 during movement from the initial position to the retracted position.

During administration of an injection to a patient, the application of force by the user in the distal direction causes the guide element 52 of retractable sheath 50 to move in a proximal direction such that guide element switches from the first guide path of the housing body to an angled second guide path of the housing body. Rotation of the retractable sheath 50 from the initial position to the retracted position transfers the guide element 52 of the retractable sheath from the first guide path 30 on the housing body 23 to the third guide path 34 on the housing body via the second guide path 32. In or more embodiments, the retractable sheath translates from the initial position to the retracted position without impediment.

As shown in FIGS. 3-6, a continued application of force by the user in the distal direction causes rotational movement of rotation cam 80 causing guide element 52 to move from the second guide path of the housing body to a third guide path thus activating the first locking element 60. In one or more embodiments, the first locking element 60 includes a tab on a proximal end of the retractable sheath. In one or more embodiments, the first locking element 60 further includes a locking rib 62 on the housing. In one or more embodiments, the first locking member may comprise a locking rib on a distal end of the retractable sheath and a tab on the housing. Movement of the retractable sheath from the initial position to the retracted position engages the locking rib of the housing to the tab on the distal end of the retractable sheath. In some embodiments the first locking element 60 is positioned at least partially within an opening included in the housing body 23. In some embodiments, the first locking element 60 is generally resilient, so that the radially inwardly disposed second ends can flex and then return to the original position even after the ends have been radially outwardly deflected. In some embodiments, the first end is larger than the second end, e.g. the axial locking member can taper from the first end to the second end 54. In one or more embodiments, the first locking member may include a latching member, such as a hook, clasp, detent, ratchet, or other structure.

Upon activating the first locking member, a locking rib of the housing engages to a tab on the distal end of the retractable sheath thereby preventing further rotational movement of the rotation cam and therefore ensuring that the guide element does not return to its initial position on the first guide path. Upon continued application of force by pressing retractable sheath 50 against the skin of a patient at the location where it is desired to insert needle cannula 42, retractable sheath 50 retracts into housing 20 allowing the injection site to be penetrated by the needle tip and needle cannula. In one or more embodiments, the first locking member inhibits reuse of the device by inhibiting rotation of the retractable sheath.

Upon completion of an injection to the patient, the user withdraws the needle cannula from the patient, thus causing the stored energy of spring element 90 to allow guide element 52 of the retractable sheath 50 to proceed along the third guide path 34 to allow retractable sheath 50 to fully cover needle cannula 42 in the extended position. The spring element 90 biases the retractable sheath 50 in a distal direction to cover the distal tip 44 of needle cannula 42 causing activation of the second locking element to prevent further translational movement of the retractable sheath 50 within the housing body 23. Movement of the retractable sheath from the retracted position to the extended position engages the second locking member to a distal tip of the needle cannula.

In one or more embodiments, the second locking element 70 is disposed on the retractable sheath and rides along the needle cannula until the second locking element covers the distal tip 44 of the needle cannula 42 in the extended position. In one or more embodiments, the second locking element 70 inhibits reuse of the safety needle device 10 by inhibiting further translational movement of the retractable sheath 50 within the housing body 23. Needle cannula 42 is obscured from view when the retractable sheath is in the extended position. As shown in FIG. 8, as the injection is completed and the distal tip 44 of needle cannula 42 is pulled from injection site, the stored force of spring element 90 causes the retracting sheath 50 to extend, and at the end of the stroke, a second locking member extends over the distal tip 44 of the needle cannula 42 to lock the retractable sheath 50 thereby completing a passive safety lock-out. In one embodiment, the second locking member is a metal clip.

Spring element 90 includes a proximal end, a main body, and a distal end. In one or more embodiments, as shown in FIG. 1, spring element 90 comprises a compression or coil spring. The spring element 90 biases the retractable sheath toward the extended position.

FIG. 1 illustrates a safety needle device 10 that may be removably coupled to a standard or specially configured syringe (not shown). Although the illustrated safety needle device 10 is configured to be coupled to and removed from a syringe, the safety needle device 10 may instead be integrally formed with the syringe. The syringe is generally of a known type suitable for the withdrawal and injection and/or aspiration of fluids or other solutions by way of the safety needle device 10. In one or more embodiments, the safety needle device is a single use device. In one or more embodiments, the safety needle device is a passively activated device in which the safety features provide post-injection needle shielding without additional intervention by the user.

Referring now to FIG. 2, the safety needle device 10 is illustrated in an initial state wherein the retractable sheath 50 is in a partially retracted configuration. Further retraction of the retractable sheath 50 is generally initiated by a user applying pressure on the safety needle device 10 and/or syringe in the distal direction, which thereby encourages the retractable sheath 50 proximally against the bias of the spring element 90. This retraction of the retractable sheath 50 in turn further exposes the distal tip 44 of the needle cannula 42 and initiates penetration by the needle cannula 42 into the patient's skin. The guide element 52 of the housing 20, which is initially positioned in the first guide path 30, directs the retractable sheath 50 to immediately move toward the second guide path 32. As the retractable sheath 50 moves proximally, the guide element 52 passes through the second guide path 32 thereby encouraging the retractable sheath 50 to rotate on the rotating cam about the axis. Upon reaching the intersection of the second and third guide paths, the guide element 52 may not return to the first guide path 30 due to the rotating cam engaging the first locking member such that a locking rib of the housing engages the tab on the distal end of the retractable sheath to prevent further rotation of the rotating cam and thus preventing the guide member from returning to the first guide path 30.

In one or more embodiment, spring element 90 engages and extends between the proximal end of the retractable sheath and the proximal end of the housing. The spring biases the retractable sheath 50 toward an initial position in which the guide element 52 of the retractable sheath 50 is biased into engagement with the first guide path located at the distal end of the housing body 23 allowing the distal tip 44 of the needle cannula 42 to be exposed and visible in the initial position. The retractable sheath 50 completely covers the distal tip 44 of the needle cannula 42 in the extended position. Many types of springs may be employed, such as but not limited to a helical coil spring, conical spring, wave-spring, Belleville washer, or the like. In some embodiments, the spring element 90 is configured to facilitate retraction of the retractable sheath 50 by a user applying distal pressure to the syringe and/or the safety needle device 10 with just one hand.

In one or more embodiments, as shown in FIGS. 3, 4, 5 and 6, rotating cam 80 includes having an outwardly extending portion from which an impeding member, such as a tab or other resilient member, extends, e.g. circumferentially, radially, axially, a combination thereof, or the like. In one or more embodiments, the end of the impeding member of the rotating cam may be shaped as a radially outwardly extending wedge having an inclined face or flat face which interacts with a wedge-shaped rotational locking member, e.g. an axial rib, extends radially inwardly from the inner surface of the housing and includes an inclined face and a generally flat face. In one or more embodiments, the inclined face of the wedge may be configured to be in the opposite direction as the inclined face. The end and rotational locking member may be wedge-shaped, hemispherical, frusto-conical, or the like. In some embodiments, the axial length of the rotational locking member is greater than the axial length of the impeding member. In some embodiments, at least a portion of the impeding member is configured to fit into at least a portion of the rotational locking member or vice versa. For example, the impeding member can comprise a tab configured to fit within a slot included in the rotational locking member.

Safety needle device 10, and components thereof, can be formed using many manufacturing processes sufficient to provide the desired shape of the components. In some embodiments one or more components are made by a molding process, such as but not limited to injection molding, compression molding, blow molding, transfer molding, or similar. In some embodiments, one or more components are formed by forging, machining, casting, stamping, extrusion, a combination thereof, or the like.

In many embodiments, the safety needle device 10 is constructed from a biocompatible material. In some arrangements one or more of the components of the safety needle device 10 are plastic (e.g. polyurethane, etc.) or metal (e.g., stainless steel, etc.). In some embodiments, the housing 20 and/or the retractable sheath 50 are constructed of materials that are either translucent or opaque.

In some embodiments, movement of the retractable sheath 50 automatically engages a first locking element 60 and second locking element 70. In some embodiments, movement of the retractable sheath 50 from an about fully retracted position to an about fully extended position automatically prevents or inhibits reuse of the safety needle device 10.

In some embodiments, the safety needle device may manufactured by forming the housing 20 with the needle support 41, the distal opening 24, the first guide path 30, second guide path 32 and third guide path 34. In embodiments in which housing 20 comprises multiple pieces, the manufacturing process can include the step of assembling the housing 20. A retractable sheath is formed having guide element 52 which is aligned with first guide path 30. The retractable sheath 50 is slidingly moved through the distal opening 24. The needle cannula 42 is coupled with the needle support 41 of the housing 20. The spring element 90 is inserted into the housing body 23 and positioned to bias the retractable sheath 50.

Figure 7:
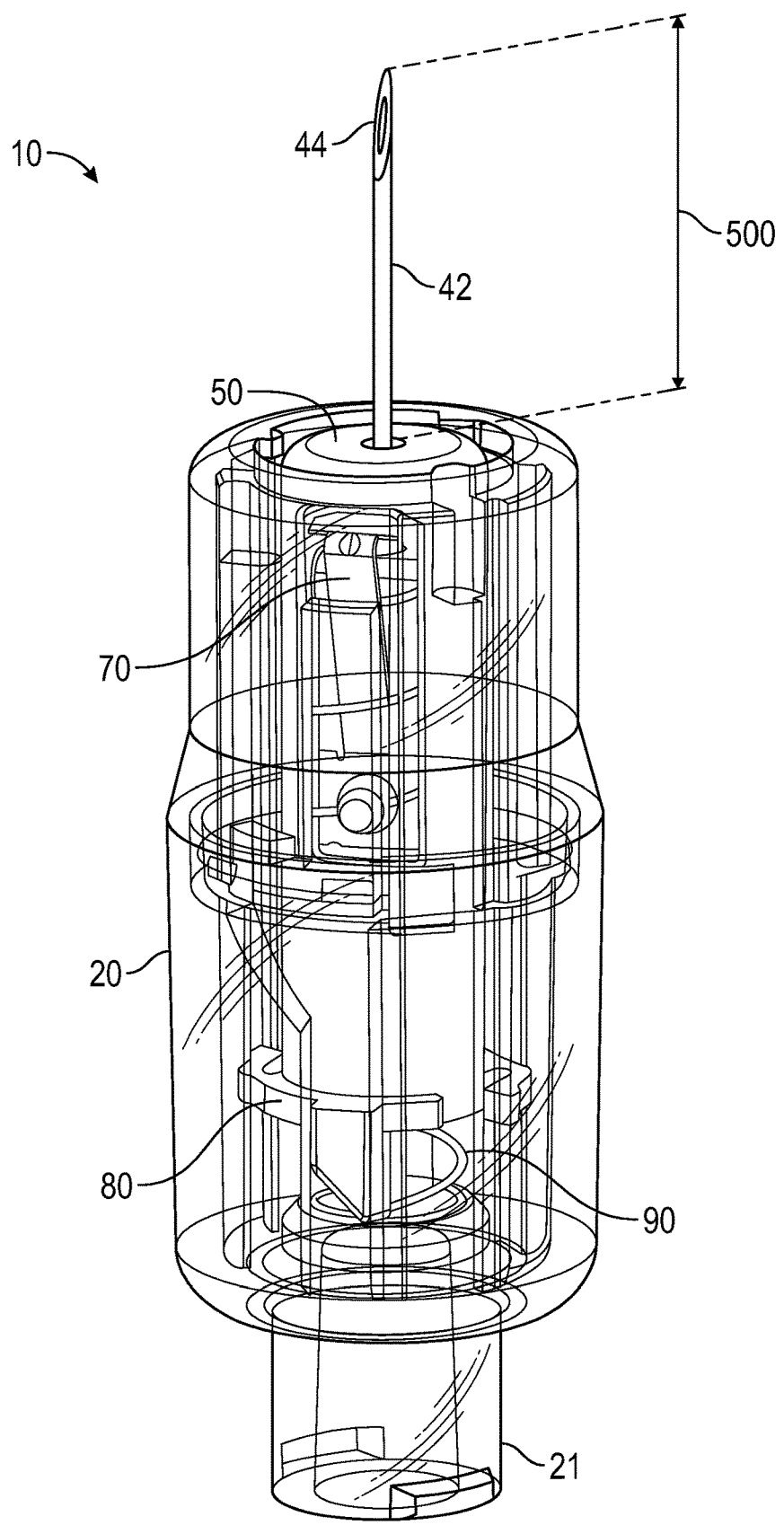
FIG. 7 illustrates a perspective view of a safety needle device shown in FIG. 1 in a retracted state.

As shown in FIG. 7, as the retractable sheath 50 continues to retract into the housing body 23, to further expose the needle cannula 42 to a length 500, the guide element 52 shifts from the second guide path 32 to the third guide path 34, thus further rotating the retractable sheath 50 with respect to the housing 20. Upon withdrawal of the needle cannula 42 from the patient, the stored spring energy of the spring element 90 to distally extend the retractable sheath 50. As the retractable sheath 50 distally extends, it covers the needle cannula 42 into the channel of the hub body thereby covering the distal end of the needle cannula 42. The distal movement of the retractable sheath 50 also slides the guide element 52 along the third guide path 34. The engagement of the first locking member inhibits or prevents counter-rotation of the retractable sheath 50, which in turn prevents the guide element 52 from shifting back into the first guide path 30 at intersection between the first guide path 30 and the second guide path 32.

As shown in FIG. 8, upon reaching the retractable sheath 50 reaching the distal tip 44 of the needle cannula 42, the second locking element 70 moves distally over the distal tip to cover the distal tip 44 of the needle cannula 4 to prevent reuse of the safety needle device 10. The retractable sheath 50 has been fully extended and fully covers the needle cannula 42. The second locking element 70 thus presents a physical stop to inhibit the retractable sheath 50 from being proximally retracted again.

Housing 20 couples to retractable sheath 50 to allow retractable sheath 50 to translate along and at least partially rotate about the axis.

Therefore, embodiments of the present disclosure utilize guide element 52 on the retractable sheath traveling along a first guide path 30, second guide path 32 and third guide path 34 disposed inside housing 20. Once injection begins, the guide element 52 on the retractable sheath 50 travels along the a first guide path 30, second guide path 32 and third guide path 34 rotating the retractable sheath from an initial position to a second position as it moves axially. Once rotation is completed, a first locking element 60 comprising two locking tabs at the top of the retractable sheath 50 snap into ribs within the housing 20. The two locking tabs serve to keep retractable sheath 50 from rotating back to the initial position ensuring that final lockout with second locking element 70 will occur. At this point, the user can continue to insert the needle to the desired depth in the patient and the retractable sheath 50 will move axially within the housing path. Upon removal of the needle cannula, spring element 90 within the system will push the retractable sheath 50 down the third guide path 34 to a final position and the second locking element 70 will automatically cover the distal tip 44 of the needle cannula 42 thereby passively protecting the user from needle stick injury.

Stroke length is the sum of needle cannula length and retractable sheath 50 lockout travel. The distance between proximal end of retractable sheath 50 and distal tip 44 of needle cannula 42 is a stack-up of tolerances and safety margin to insure needle stick injury (NSI) is prevented following use.

In one or more embodiments, overall length of the safety needle device may be reduced when the spring element is allowed to collapse inside both the retractable sheath 50 and housing 20. Thus reducing overall length by the solid height and subsequently lowering forces applied to a patient's skin.

In one or more embodiments, overall length of the safety needle device may also be reduced by using telescoping components.

Figure 9:
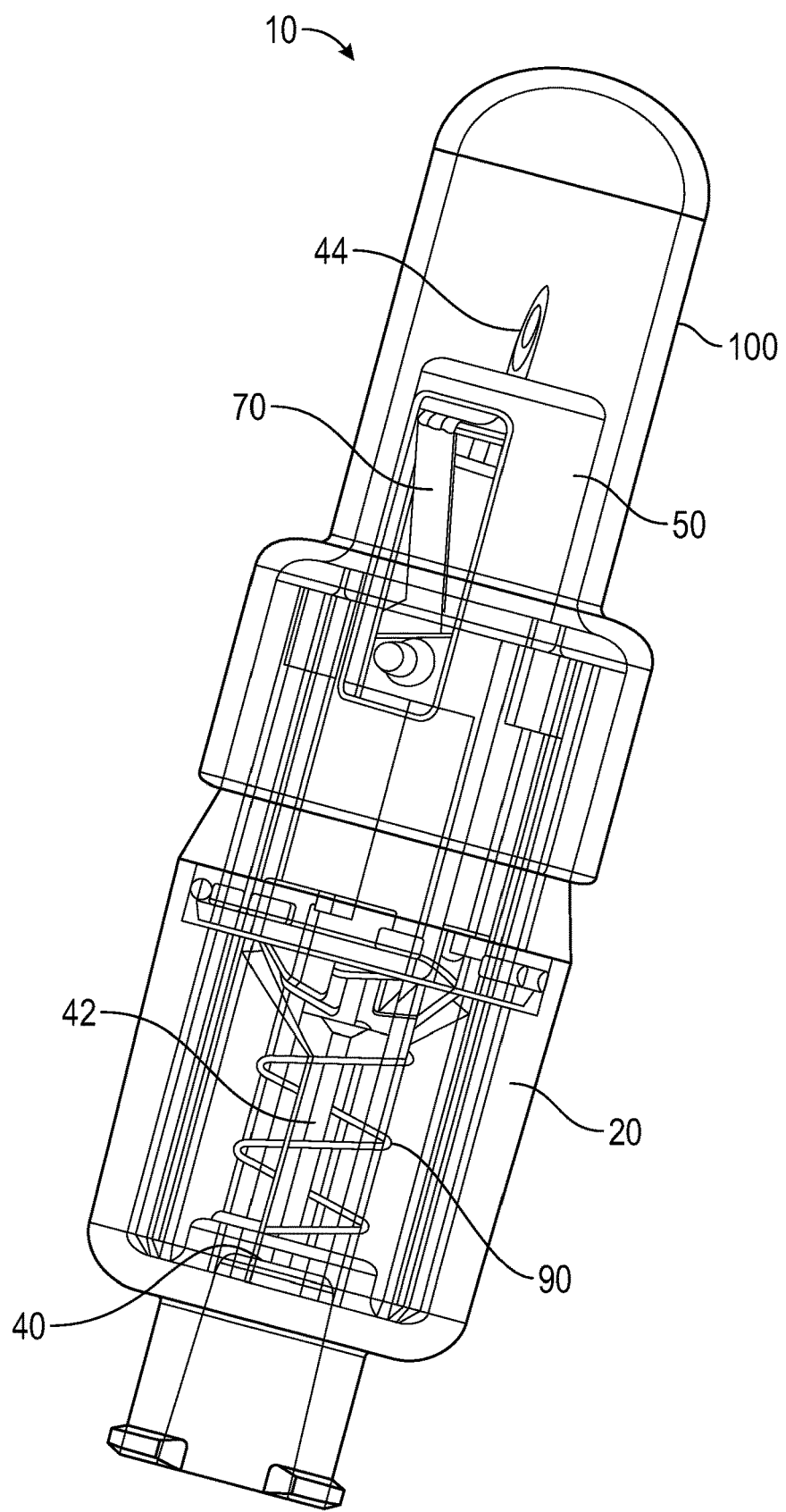
FIG. 9 illustrates a perspective view of a safety needle device according to a first embodiment.

As shown in FIG. 9, in one or more embodiments, the safety needle device 10 can include a cap 100 that is removably coupled to the housing 20 to reduce or prevent contamination of the needle cannula during shipping and storage of the safety needle device 10. The cap 100 is generally kept in the closed position until just prior to an injection and/or aspiration procedure, at which time the cap 100 removed from the housing 20. In some embodiments, cap 100 is configured to assist in properly drawing a dose from a vial.

Any suitable caps or packaging comprising a safety feature may be used in conjunction with the safety needle device disclosed herein. Any suitable caps or packaging comprising a safety feature may be used in conjunction with the safety needle device disclosed herein. Types of safety features vary in structure and mechanics but exemplary caps or packaging include, but are not limited to, those described in commonly owned, U.S. Patent Application Ser. Nos. 62/433,044, 62/433,526 and 62/433,297, the disclosures of which are incorporated herein by reference in their entireties.

Reference throughout this specification to "one embodiment," "certain embodiments," "various embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in various embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein provided a description with reference to particular embodiments, it is to be understood that these embodiments are merely illustrative of the principles and applications of the disclosure. It will be apparent to those skilled in the art that various modifications and variations can be made to the present disclosure without departing from the spirit and scope thereof. Thus, it is intended that the present disclosure include modifications and variations that are within the scope of the appended claims and their equivalents.

What is claimed is:

1. A safety needle device, comprising:
   a housing configured to couple to a syringe, the housing having a proximal end, a distal end, and a housing body;
   a first guide path, a second guide path and a third guide path disposed on the housing body, the second guide path intersecting the first guide path and the third guide path, the first guide path located at the distal end of the housing body;
   a needle hub disposed on the proximal end of the housing;
   a needle cannula attached to the needle hub, the needle cannula having a distal tip;
   a retractable sheath having a guide element configured to move between an initial position, a retracted position and an extended position with respect to the housing, wherein the retractable sheath rotates with respect to the housing during movement from the initial position to the retracted position, wherein the guide element is biased into engagement with the first guide path allowing the distal tip of the needle cannula to be exposed in the initial position;
   a first locking element, the first locking element comprising a tab on a distal end of the retractable sheath and a locking rib on the housing;
   a second locking element;
   a rotating cam disposed in the housing body; and
   a spring element;
   wherein movement of the retractable sheath from the initial position to the retracted position engages the locking rib of the housing to the tab on the distal end of the retractable sheath, thereby preventing further rotation of the rotating cam and thus preventing the guide element from returning to the first guide path.

2. The safety needle device of claim 1, wherein the guide element extends radially outward from a proximal end of the retractable sheath.

3. The safety needle device of claim 1, wherein the first locking element is tapered.

4. The safety needle device of claim 1, wherein the first locking element is passively activated.

5. The safety needle device of claim 1, wherein rotation of the retractable sheath from the initial position to the retracted position transfers the guide element of the retractable sheath from the first guide path on the housing to the third guide path on the housing via the second guide path.

6. The safety needle device of claim 1, wherein the second locking element comprises a metal latch.

7. The safety needle device of claim 1, wherein the second locking element is passively activated.

8. A safety needle device of claim 1, wherein movement of the retractable sheath from the retracted position to the extended position engages the second locking element to the distal tip of the needle cannula.

9. The safety needle device of claim 1, wherein the first locking element inhibits reuse of the safety needle device by inhibiting rotation of the retractable sheath.

10. The safety needle device of claim 1, wherein the second locking element inhibits reuse of the safety needle device by inhibiting translation of the retractable sheath.

11. The safety needle device of claim 1, wherein the spring element biases the retractable sheath toward the extended position.

12. The safety needle device of claim 1, wherein the retractable sheath translates from the initial position to the retracted position without impediment.

13. The safety needle device of claim 1, wherein the needle cannula is obscured from view when the retractable sheath is in the extended position.

14. The safety needle device of claim 1, wherein the initial position partially exposes a distal tip of the needle cannula, the retracted position fully exposes the needle cannula, and the extended position fully covers the distal tip of the needle cannula, the first guide path and the second guide path disposed on the housing body configured to receive the guide element.

15. The safety needle device of claim 1, further comprising a cap removably coupled to the housing.

16. A safety needle device, comprising:
   a housing configured to couple to a syringe, the housing having a proximal end, a distal end, and a housing body;
   a first guide path, a second guide path and a third guide path disposed on the housing body, the second guide path intersecting the first guide path and the third guide path;
   a needle hub disposed on the proximal end of the housing;
   a needle cannula attached to the needle hub, the needle cannula having a distal tip;
   a retractable sheath having a guide element configured to move between an initial position, a retracted position and an extended position with respect to the housing, wherein the retractable sheath rotates with respect to the housing during movement from the initial position to the retracted position, wherein the guide element is biased into engagement with the first guide path allowing the distal tip of the needle cannula to be exposed in the initial position;
   a locking rib on a distal end of the retractable sheath;
   a tab on the housing;
   a metal latch disposed on the retractable sheath;
   a rotating cam disposed in the housing body; and
   a spring element.

17. The safety needle device of claim 16, wherein the spring element is a coil spring.

18. The safety needle device of claim 16, further comprising a cap removably coupled to the housing.

* * * * *